United States Patent [19]
Bechard

[11] Patent Number: 5,431,920
[45] Date of Patent: Jul. 11, 1995

[54] ENTERIC COATED ORAL COMPOSITIONS CONTAINING BISPHOSPHONIC ACID ANTIHYPERCALCEMIC AGENTS

[75] Inventor: Simon R. Bechard, Laval, Canada

[73] Assignee: Merck Frosst, Canada, Inc., Kirkland, Canada

[21] Appl. No.: 125,372

[22] Filed: Sep. 21, 1993

[51] Int. Cl.$^6$ ............................. A61K 9/36; A61K 9/16
[52] U.S. Cl. ................................... 424/480; 424/470; 424/481; 424/482; 424/490; 424/494; 424/495; 424/496; 424/497; 514/89; 514/91; 514/107; 514/108; 514/951; 514/960; 514/961
[58] Field of Search ............... 424/470, 480, 481, 482, 424/490, 494, 495, 496, 497; 514/781, 951, 960, 89, 91, 107, 108, 961

[56] References Cited

U.S. PATENT DOCUMENTS

| | | | |
|---|---|---|---|
| 4,054,598 | 10/1977 | Blum et al. | 260/502.5 |
| 4,113,861 | 9/1978 | Fleish et al. | 424/204 |
| 4,137,309 | 1/1979 | Van Duzee | 424/204 |
| 4,267,108 | 5/1981 | Blum et al. | 260/326.61 |
| 4,621,077 | 11/1986 | Rosini et al. | 514/108 |
| 4,624,947 | 11/1986 | Blum et al. | 514/108 |

FOREIGN PATENT DOCUMENTS

93/09785  5/1993  WIPO.

Primary Examiner—Jyothsna Venkat
Attorney, Agent, or Firm—Joanne M. Giesser; Melvin Winokur; Joseph F. DiPrima

[57] ABSTRACT

The present invention relates to a novel oral dosage form of a bisphosphonic active ingredient for use in treatment of diseases involving bone resorption and formulated in an enteric-coated form for administration to subjects exhibiting upper gastrointestinal tract sensitivity to bisphosphonic acid compounds.

7 Claims, No Drawings

ENTERIC COATED ORAL COMPOSITIONS CONTAINING BISPHOSPHONIC ACID ANTIHYPERCALCEMIC AGENTS

SUMMARY OF THE INVENTION

The present invention relates to a novel oral dosage form of a bisphosphonic active ingredient for use in treatment of diseases involving bone resorption and formulated in an enteric-coated form for administration to subjects exhibiting upper gastrointestinal tract sensitivity to bisphosphonic acid compounds. Said novel dosage form consists of a core tablet containing a therapeutically effective amount of a bisphosphonic acid active ingredient which is subcoated with a polymeric film having the effect of preventing migration of active ingredient from core tablet to the outer enteric coating. This subcoat improves product stability by minimizing drug interaction with the acidic enteric coating and also permits application of an enteric coating sufficiently thin to rapidly and completely dissolve upon entry into the proximal portion of the lower gastrointestinal tract.

BACKGROUND OF THE INVENTION

The bisphosphonates are a new class of drags which have been developed during the past two decades for diagnostic and therapeutic use in various diseases of bone and calcium metabolism. Papapoulos describes therapeutic bisphosphonates as falling into three categories: first generation drugs typified by etidronate, which have significant activity but do not predictably suppress bone resorption; second generation agents such as pamidronate which cause predictable resorption suppression when given parenterally, but are hampered in oral formulations by low absorption and GI toxicity, and a third generation with both oral and parenteral efficacy. Fleisch indicates that bisphosphonate compounds are the drugs of choice in tumor induced bone disease and that the relatively few adverse events that have been associated with their use are specific for each compound.

The three compounds commercially available for use in tumor induced bone disease are in order of increasing potency, 1-Hydroxyethylidene-bisphosphonic acid (etidronate), Dichloromethylene-bisphosphonic acid (clodronate), and 3-Amino-1-hydroxypropylidene-bisphosphonic acid (pamidronate). Other bisphosphonate compounds known in literature to have been administered to humans include 4-Amino-1-hydroxybutylidene-bisphosphonic acid (alendronate), 6-Amino-1-hydroxyhexylidene-bisphosphonic acid, (4-Chlorophenyl)thiomethylidene-bisphosphonic acid (tiludronate), 2-(3-pyridinyl)-1-hydroxyethylidene-bisphosphonic acid (risedronate), and 1-Hydroxy-3-(methylpentylamino)-propylidene-bisphosphonic acid (BM 21.0955).

The individual bisphosphonates exhibit varying degrees of gastrointestinal toxicity. The pronounced GI toxicity of pamidronate is well documented and use of enteric coated tablets of pamidronate in clinical studies was disclosed by Reid et al. PCT Publication No. WO 93/09785 discloses enterically-coated dosage forms of the drug risedronate, one embodiment of which is a compressed tablet of active ingredient directly coated with a single layer of enteric polymer. The absence of prior art suggesting enteric coated dosage forms for bisphosphonates other than pamidronate and risedronate may reflect lower degrees of G.I. toxicity exhibited by some of these compounds or the fact that the low absorption of some of these compounds through the gastrointestinal tract has made IV infusion the favored mode of administration. The greater antihypercalcemic activity and GI absorption of newer compounds makes oral administration increasingly attractive. Although these other bisphosphonates may not exhibit the same degree of GI toxicity as pamidronate, they nonetheless may produce gastric irritation in particularly sensitive individuals. Enteric-coated dosage forms for these other bisphosphonate compounds may provide a solution to this problem. In order to maximize absorption of active, it is desirable that such a dosage form release the active in the proximal portion of the lower G.I. tract, preferably in the small intestine. This requires that the enteric film be soluble at pH 5.5 or greater as typically present in the small and large intestines. Enteric coated dosage forms can suffer from stability problems as a result of interactions between the active drug and the acidic enteric coating. In particular, bisphosphonate compounds which have a basic nitrogen containing moiety are susceptible to interaction with acidic carboxyl groups present in the enteric coating polymer. The present invention solves the above problems by providing a novel enteric-coated dosage form comprising a core tablet containing a therapeutically effective amount of bisphosphonate, a stability enhancing subcoat which minimizes migration of active from core tablet to the surface of the enteric coating, and an enteric film specifically formulated to rapidly and completely dissolve once the dosage form enters the proximal portion of the lower gastrointestinal tract.

DETAILED DESCRIPTION OF THE INVENTION

This invention relates to a novel enteric-coated dosage form of a bisphosphonic acid active ingredient adapted for oral administration to subjects suffering from metabolic bone diseases (e.g. osteoporosis) including those associated with abnormal calcium metabolism e.g. hypercalcemia and exhibiting upper gastrointestinal tract sensitivity to bisphosphonic acid. Said dosage forms comprise a pH dependent enteric film formulated to rapidly and completely dissolve upon exposure to intestinal fluids having a pH of 5.5 or greater, and a stability enhancing polymeric subcoat deposited on a core tablet containing the bisphosphonate active ingredient. Dosage forms of this invention prohibit the release of active ingredient in the mouth, esophagus, and stomach and thereby protect mucosal tissues thereof from irritation that may result from exposure to bisphosphonic acid compounds. Accordingly, the said dosage form effects the delivery to the proximal portion of lower intestinal tract of a safe and effective amount of bisphosphonic acid active ingredient while minimizing irritation of the mouth, esophagus, and stomach that may accompany the oral administration of bisphosphonic acid compounds.

A. The Bisphosphonate Active Ingredient

The scope of this invention covers those bisphosphonic acid compounds corresponding to structural formula (I)

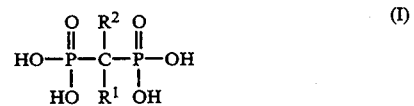

or a pharmaceutically acceptable salt thereof, wherein:
$R^1$ is
- (a) —$C_{1-5}$ alkyl, unsubstituted or substituted with:
  - (1) —$NH_2$,
  - (2) pyridyl,
  - (3) pyrrolidyl, or
  - (4) —$NR^3R^4$,
- (b) —$NHR^5$,
- (c) —$SR_6$, or
- (d) —Cl;

$R^2$ is —H, —OH, or —Cl;
$R^3$ is —H, or —$C_{1-5}$ alkyl;
$R^4$ is —$C_{1-5}$ alkyl;
$R^5$ is —$C_{1-10}$ alkyl or —$C_{3-10}$ cycloalkyl;
$R^6$ is aryl, unsubstituted or substituted.

As used herein, "alkyl" is intended to include both branched- and straight-chain saturated aliphatic hydrocarbon groups having the specified number of carbon atoms; "cycloalkyl" is intended to include saturated ring groups, such as cyclopropyl, cyclobutyl, cyclopentyl, cyclohexyl (Cyh) and cycloheptyl. "Aryl" is intended to mean aromatic groups such as, e.g., phenyl and naphthyl, which may be unsubstituted or substituted. Aryl may be substituted with, e.g., one or more of halogen (fluoro, chloro, bromo and iodo), nitro, amino, $C_{1-4}$alkyl, $C_{1-4}$alkoxy, or trifluoromethyl.

Methods for the preparation of various bisphosphonic acid compounds may be found in, e.g., U.S. Pat. No. 3,962,432; U.S. Pat. No. 4,054,598; U.S. Pat. No. 4,327,039; U.S. Pat. No. 4,621,077; U.S. Pat. No. 4,746,654; U.S. Pat. No. 4,267,108; U.S. Pat. No. 4,407,761; U.S. Pat. No. 4,624,947; U.S. Pat. No. 4,922,077; and EPO Patent Pub. No. 0,252,504.

A particular illustration of the present invention is the novel dosage form thereof in which the bisphosphonic acid active ingredient is 4-Amino-1-hydroxybutylidene-1,1-bisphosphonic acid (alendronate). Further exemplifying the present invention is the novel dosage form thereof containing the sodium salt of 4-Amino-1-hydroxybutylidene-1,1-bisphosphonic acid, in particular 4-Amino-1-hydroxybutylidene-1,1-bisphosphonic acid monosodium salt trihydrate. Studies indicate that, when parenterally administered, this compound is about five times more effective in reducing hypercalcemia associated with tumor induced bone disease in humans than pamidronate, the most potent bisphosphonate commercially available for treatment of tumor induced bone disease. 4-Amino-1-hydroxybutylidene-1,1-bisphosphonic acid and its homologs in which the $R^1$ side chain is a N-alkyl group varying in length from 1 to 5 carbon atoms and terminally substituted with an amino group may be readily synthesized according to methods disclosed in U.S. Pat. Nos. 4,407,761, and 4,922,007. In addition to the mono, di, and trisodium salts, other pharmaceutically acceptable salts of bisphosphonic acids that may be employed in the present invention include ammonium salts, alkali metal salts such as potassium, alkaline earth metal salts such as calcium and magnesium salts, salts with organic bases such as dicyclohexylamine salts, N-methyl-D-glucamine, and salts with amino acids such as arginine, lysine and so forth. The salts may be prepared by methods known in the art, such as in U.S. Pat. No. 4,922,077.

B. Novel Enteric-Coated Oral Dosage Form For Delivery of the Bisphosphonic Acid Active Ingredient to the Lower Intestine As stated hereinabove, the present invention is directed to a novel enteric-coated oral dosage form of the bisphosphonic acid active ingredient to effect delivery to the lower intestine of a human or other mammal, preferably to the small intestine, of a pharmaceutical composition comprised of a therapeutically effective amount of about 0.1–500 mg of a bisphosphonic acid active ingredient and pharmaceutically accepted excipients.

The term "pharmaceutically-acceptable excipients" as used herein includes any physiologically inert, pharmacologically inactive material known to one skilled in the art, which is compatible with the physical and chemical characteristics of the particular bisphosphonic acid selected for use.

CORE TABLETS

Core tablets of the present invention may be formed by combining the bisphosphonic acid active ingredient with pharmaceutically-acceptable excipients in a mixture including, but not limited to:
- a diluent,
- a binder,
- a disintegrant,
- and optionally one or more ingredients selected from a group consisting of: compression aids, flavors, flavor enhancers, sweeteners, dyes, pigments, buffer systems, and preservatives;

lubricating the mixture with a lubricant; and compressing the resultant lubricated mixture into a desired tablet form using various tableting techniques available to those skilled in the art. The term "tablet" as used herein is intended to encompass compressed pharmaceutical dosage formulations of all shapes and sizes.

Particular diluents employable in the present invention include, but are not limited to, lactose. In particular anhydrous lactose is preferred.

Particular binders employable in the present invention include, but are not limited to, microcrystalline cellulose. Micro-crystalline cellulose is available under the trade name "Avicel" from FMC Corporation.

The disintegrant may be one of several modified starches, or modified cellulose polymers, in particular, crosscarmellose sodium is preferred. Crosscarmellose sodium NF Type A is commercially available under the trade name "Ac-di-sol".

Particular lubricants employable in the present invention include, but are not limited to, magnesium stearate, stearic acid, and talc.

Flavoring agents among those useful herein include those described in *Remington's Pharmaceutical Sciences*, 18th Edition, Mack Publishing Company, 1990, pp. 1288–1300.

Particular sweeteners employable in the present invention include but are not limited to sucrose, saccharin, glucose, and aspartame.

Dyes and pigments among those useful include those described in the *Handbook of Pharmaceutical Excipients*, pp. 81–90, 1986 by the American Pharmaceutical Association & the Pharmaceutical Society of Great Britain.

Particular preservatives employable in the present invention include, but are not limited to methyl paraben, propyl paraben, cetylpyridinium chloride, and the salts thereof, sorbic acid and the salts thereof, thimerosal, and benzalkonium chloride.

Although core tablets of the present invention may be prepared using conventional technology and pharmaceutically-acceptable excipients, standard methods for tablet formulation of bisphosphonic acids suffer from serious difficulties. In particular, bisphosphonic acids which bear a basic nitrogen-containing moiety may interact with the lactose of standard formulations resulting in instability and loss of potency. This degradation is particularly pronounced in the presence of water. The U.S. Pat. No. 5,358,941 corresponding to Ser. No. 07/984,399 discloses a dry mix formulation for tablets containing bisphosphonic acids and a process for the preparation of such tablets which eliminates the above mentioned problems by avoiding interaction between the bisphosphonic acid and lactose in the formulation. This process is preferred for preparation of core tablets in the present invention.

ENTERIC COATING

The term "enteric-coating" as used herein relates to a mixture of pharmaceutically acceptable excipients which is applied to the core tablet containing the bisphosphonic acid active ingredient and which prevents release of said active ingredient in the mouth, esophagus or stomach, but which rapidly and completely releases the drug when the dosage form passes into the proximal portion of the lower gastrointestinal tract.

Any conventional enteric film forming polymer or mixture of polymers which is insoluble at a pH below 5.5, i.e., that generally found in the mouth, esophagus, and stomach, but soluble at pH 5.5 or above, i.e., that present in the small intestine and the large intestine, can be used in the present invention.

Particular enteric film forming polymers employable in the present invention include but are not limited to cellulose acetate phthalate, methyl acrylate-methacrylic acid copolymers, cellulose acetate succinate, hydroxypropylmethylcellulose phthalate, polyvinyl acetate phthalate, and methyl methacrylate-methacrylic acid copolymers.

Of these, we particularly prefer to use anionic carboxylic copolymers based on methacrylic acid and methacrylate, commercially available as Eudragit ®. A particularly suitable methacrylic acid copolymer is Eudragit L-30-D ®, manufactured by Rohm Pharma GmbH, Weiterstadt, West Germany. Eudragit L-30-D ® has a ratio of free carboxyl groups to ester groups of approximately 1:1 and is freely soluble at pH 5.5 and above as typically present in the small intestine and the large intestine. In general, the greater the percentage of Eudragit L-30-D ® contained in the enteric coating of the present invention, the more proximal the release of active in the lower gastrointestinal tract. The location in the lower gastrointestinal tract at which said coatings release the active can be manipulated by one skilled in the art through control of the composition and thickness of the applied enteric coating.

In order to function properly as an enteric coating, the polymer film must be essentially free from pores or cracks which would permit penetration of the gastric fluids. The propensity of the film to crack is reduced by using a plasticizer. Although the nature of such plasticizers is restricted by the requirement that they should be safe to administer to mammalian organisms, a wide range of compounds may be used as a plasticizer in practice of the present invention.

Particular plasticizing agents employable in the present invention include, but are not limited to propylene glycol, glycerol, glyceryl triacetate, polyethylene glycol, triethyl citrate, tributyl citrate, diethyl phthalate, and dibutyl phthalate.

Other additives such as talc or silica may be used as detackifiers to improve the coating process.

SUBCOATING

In order to rapidly and completely deliver the bisphosphonic acid active ingredient to the proximal portion of the lower gastrointestinal tract, preferably the small intestine, it is important that the enteric film not be so thick as to impede complete dissolution and release of the active ingredient in the small intestine.

The novel enteric-coated dosage forms embodied in the present invention may incorporate a stability enhancing subcoat which in addition to minimizing interaction between active drug and the acidic enteric coating also permits utilization of a single 10–300 micron thick enteric film without compromising product stability. This subcoat inhibits migration of active ingredient from core tablet to the enteric coating, thus improving shelf life and product stability, but rapidly dissolves in intestinal fluid once the enteric coating has been breached.

Particular subcoating polymers employable in the present invention include, but are not limited to hydroxypropyl methylcellulose, hydroxypropyl cellulose, hydroxypropyl ethylcellulose, and polyvinylpyrrolidone.

The following are specific embodiments to teach the practice of the disclosed invention but not to limit its scope. For these specific examples, alendronate monosodium trihydrate is used as the therapeutic bisphosphonate compound incorporated in the core tablet. The amount of alternative bisphosphonate compounds would, of course, be adjusted according to the relative potency and therapeutic effectiveness of the particular compound. The amounts of the enteric-coating components would therefore be adjusted so that a thin, 10–300 micron film of the enteric coating polymer can be uniformly applied over the surface of the tablets. All film coats are atomized and deposited onto the core tablets from aqueous dispersions containing between 1–40% solids using conventional pharmaceutical technology.

EXAMPLE 1

|  | mg alendronate/tablet | | |
|---|---|---|---|
|  | 5 mg | 25 mg | 50 mg |
| Subcoat | | | |
| Hydroxypropyl Methylcellulose 6 cP | 4.0 | 4.0 | 6.0 |
| Functional Coating | | | |
| Eudragit L30D (methacrylic acid copolymer, type C, NF) | 12.1 | 12.1 | 18.1 |
| Triacetin, USP | 1.3 | 1.3 | 2.0 |
| Polyethylene Glycol, USP | 2.0 | 2.0 | 3.0 |
| Talc, USP | 2.4 | 2.4 | 3.6 |
| Xantham Gum, NF | 0.2 | 0.2 | 0.3 |
| FUNCTIONAL FILM WEIGHT: | 18.0 mg | 18.0 mg | 27.0 mg |

EXAMPLE 2

|  | mg alendronate/tablet | | |
|---|---|---|---|
|  | 5 mg | 25 mg | 50 mg |
| Subcoat | | | |
| Hydroxypropyl Methylcellulose 6 cP | 4.0 | 4.0 | 6.0 |
| Functional Coating | | | |
| Eudragit L30D (methacrylic acid copolymer, type C, NF) | 12.7 | 12.7 | 19.0 |
| Polyethylene Glycol 400 | 1.3 | 1.3 | 2.0 |
| FUNCTIONAL FILM WEIGHT: | 14.0 mg | 14.0 mg | 21.0 mg |

EXAMPLE 3

|  | mg alendronate/tablet | | |
|---|---|---|---|
|  | 5 mg | 25 mg | 50 mg |
| Subcoat | | | |
| Hydroxypropyl Methylcellulose 6 cP | 4.0 | 4.0 | 6.0 |
| Functional Coating | | | |
| Eudragit L30D (methacrylic acid copolymer, type C, NF) | 12.7 | 2.7 | 19.0 |
| Polyethylene Glycol 3350 | 2.0 | 2.0 | 3.0 |
| FUNCTIONAL FILM WEIGHT: | 14.7 mg | 14.7 mg | 22.0 mg |

EXAMPLE 4

|  | mg alendronate/tablet | | |
|---|---|---|---|
|  | 5 mg | 25 mg | 50 mg |
| Subcoat | | | |
| Hydroxypropyl Methylcellulose 6 cP | 4.0 | 4.0 | 6.0 |
| Functional Coating | | | |
| Eudragit L30D (methacrylic acid copolymer, type C, NF) | 12.7 | 12.7 | 19.0 |
| Triethylcitrate | 1.3 | 1.3 | 2.0 |
| FUNCTIONAL FILM WEIGHT: | 14.0 mg | 14.0 mg | 21.0 mg |

EXAMPLE 5

|  | mg alendronate/tablet | | |
|---|---|---|---|
|  | 5 mg | 25 mg | 50 mg |
| Subcoat | | | |
| 50:50 Hydroxypropyl Methylcellulose/ Hydroxypropyl cellulose | 4.0 | 4.0 | 6.0 |
| Functional Coating | | | |
| Eudragit L30D (methacrylic acid copolymer, type C, NF) | 12.7 | 12.7 | 19.0 |
| Triethylcitrate | 1.3 | 1.3 | 2.0 |
| FUNCTIONAL FILM WEIGHT: | 14.0 mg | 14.0 mg | 21.0 mg |

EXAMPLE 6

|  | mg alendronate/tablet | | |
|---|---|---|---|
|  | 5 mg | 25 mg | 50 mg |
|  | 4.0 | 4.0 | 6.0 |
| Enteric Coating | | | |
| Eudragit L30D (methacrylic acid copolymer, type C, NF) | 12.1 | 12.1 | 18.1 |
| Triacetin, USP | 1.3 | 1.3 | 2.0 |
| Polyethylene Glycol, USP | 2.0 | 2.0 | 3.0 |
| Talc, USP | 2.4 | 2.4 | 3.6 |
| Xantham Gum, NF | 0.2 | 0.2 | 0.3 |
| FUNCTIONAL FILM WEIGHT: | 18.0 mg | 18.0 mg | 27.0 mg |

From the foregoing, other typical acceptable pharmaceutical formulations will be apparent to those skilled in the art of pharmaceutical formulations. While this invention has been described and illustrated with reference to certain preferred embodiments thereof, those skilled in the art will appreciate that various changes, modifications and substitutions can be made therein without departing from the spirit of the inven-

What is claimed is:

1. An enteric-coated oral dosage form comprising:
   (i) a core tablet or granules containing a therapeutically effective amount of a bisphosphonic acid compound having the formula (I)

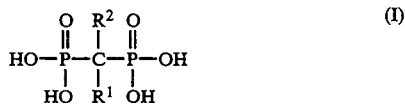

or a pharmaceutically acceptable salt thereof, wherein:
   $R^1$ is
   (a) —$C_{1-5}$ alkyl, unsubstituted or substituted with:
      (1) —$NH_2$,
      (2) pyridyl,
      (3) pyrrolidyl, or
      (4) —$NR^3R^4$,
   (b) —$NHR^5$,
   (c) —$SR^6$, or
   (d) —Cl;
   $R^2$ is —H, —OH, or —Cl;
   $R^3$ is —H, or —$C_{1-5}$ alkyl;
   $R^4$ is —$C_{1-5}$ alkyl;
   $R^5$ is —$C_{1-10}$ alkyl or —$C_{3-10}$ cycloalkyl;
   $R^6$ is phenyl, and
   (ii) an enteric coating comprising a polymer selected from the group consisting of cellulose acetate phthalate, methyl acrylate-methacrylic acid copolymers, cellulose acetate succinate, hydroxy propyl methyl cellulose phthalate, polyvinyl acetate phthalate, and methyl methacrylate-methacrylic acid copolymers;
   (iii) a subcoat comprising a pH independent polymeric film selected from the group consisting of hydroxypropyl methyl cellulose, hydroxypropyl cellulose, hydroxypropyl ethyl cellulose, polyvinyl pyrrolidone and 50:50 mixture of hydroxypropyl methyl cellulose and hydroxy propyl cellulose, where in the polymeric film is applied to said core tablet or granule wherein said polymeric film prevents the migration of the bisphosphonic acid to the outer enteric coating.

2. The dosage form of claim 1 wherein the bisphosphonic acid active ingredient is selected from the group consisting of:
   (a) Alendronic Acid,
   (b) Etidronic Acid,
   (c) Clodronic Acid,
   (d) Pamidronic Acid,
   (e) Tiludronic Acid,
   (f) Risedronic Acid,
   (g) 6-Amino-1-hydroxyhexylidene-bisphosphonic acid,
   (h) 1-Hydroxy-3(methylpentylamino)-propylidene bisphosphonic acid;
   and a pharmaceutically acceptable salt thereof.

3. The dosage form of claim 1 wherein the amount of bisphosphonic acid active ingredient contained in the core tablet is between 0.1 and 500 mg.

4. The dosage form of claim 1 wherein the bisphosphonic acid active ingredient is the monosodium trihydrate salt of 4-Amino-1-hydroxybutylidene-1,1-bisphosphonic acid.

5. The dosage form of claim 1 wherein said enteric coating is methacrylic acid and methacrylate copolymers wherein the ratio of free carboxyl to ester is about 1:1.

6. The dosage form of claim 1 wherein said polymeric film is hydroxypropyl methylcellulose.

7. The dosage form of claim 1 wherein said polymeric film is 50:50 mixture of hydroxypropyl methylcellulose and hydroxypropyl cellulose.

* * * * *